United States Patent [19]

Cheetham

[11] 4,393,136

[45] Jul. 12, 1983

[54] BACTERIAL ETHANOL PRODUCTION

[75] Inventor: Peter S. J. Cheetham, Reading, England

[73] Assignee: Talres Development (N.A.) N.V., Netherlands Antilles

[21] Appl. No.: 281,293

[22] Filed: Jul. 7, 1981

[30] Foreign Application Priority Data

Jul. 8, 1980 [GB] United Kingdom ................. 8022243

[51] Int. Cl.³ .............................................. C12D 7/06
[52] U.S. Cl. ................................... 435/161; 435/170; 435/174; 435/177; 435/178
[58] Field of Search ............... 435/155, 161, 162, 170, 435/174, 182, 176–181

[56] References Cited

U.S. PATENT DOCUMENTS 4,167,450  9/1979  Chesbro et al. ..................... 435/3
4,272,617  6/1981  Kaetsu et al. ..................... 435/182
4,321,327  3/1982  Chen et al. ........................ 435/161

FOREIGN PATENT DOCUMENTS 54-132294  10/1979  Japan ................................. 435/174

*Primary Examiner*—Robert A. Yoncoskie
*Attorney, Agent, or Firm*—Ostrolenk, Faber, Gerb & Soffen

[57] ABSTRACT

Glucose or other substrate is converted to ethanol using immobilized bacterial cells under conditions which prevent growth of the cells.

16 Claims, No Drawings

BACTERIAL ETHANOL PRODUCTION

The present invention relates to ethanol production, and in particular to the production of ethanol using bacteria.

It is well known that yeasts can be used to produce ethanol, i.e. alcohol, from glucose or related carbohydrate substrates by a fermentation (that is, by a decomposition using the growing microorganisms). Such fermentations form the basis of the production of beer and other alcoholic drinks, and are now the subject of increasing interest with a view to producing industrial alcohol and power alcohol.

In contrast to the production of ethanol by yeasts, the production of ethanol by bacteria has received very much less study.

Strains of the bacterium Zymomonas mobilis are sometimes used in tropical countries for making alcoholic drinks, and the possible use of Zymomanas spp in the production of alcohol-containing fuels by fermenttion is under academic investigation by P. L. Rogers and others at the School of Biological Technology, University of New South Wales, Sydney, Australia. Rogers and his co-workers have reported that Z. mobilis can efficiently and rapidly ferment glucose to ethanol: in Biotechnology Letters, 1979, 1(10), 165 they report work on batch culture of Z. mobilis ATCC 10988, while in the same journal at 1(4), 421 they report work on continuous culture.

We have been investigating the industrial production of ethanol using microorganisms, and have found a novel process for producing ethanol from bacteria which process is not one of bacterial fermentation as described by Rogers et al.

According to the present invention, we provide a process for producing ethanol which process employs immobilized cells of an ethanol-producing bacterium to convert a carbohydrate or other substrate into ethanol. The substrate employed is one which could be utilized for growth by the bacterium, but growth is minimized by presenting the substrate to the immobilized bacterium as a nutritionally-deficient medium. Thus, we regard the present process as essentially relying upon non-growing cells of the bacterium.

For the present process, an ethanol-producing bacterium is immobilized by means of a suitable technique, such as entrapment within a gel. Ethanol is then produced on a bath or continuous basis by supplying carbohydrate to the immobilized bacterium but without supplying all the nutrients required for growth of the bacterium. The bacterium then effects the conversion of the carbohydrate to ethanol, acting as an immobilized enzyme system rather than as a proliferating microorganism.

Compared with the known fermentations using Zymomonas spp, the present, principally non-fermentative process has the substantial advantage that assimilated carbon does not have to be channelled into production of new cells: in principle all the carbohydrate can follow the metabolic pathway through to ethanol.

In a paper presented in March of 1980 at the "Symposium on Bioconversion and Biochemical Engineering" held in New Delhi, India, Dr. Rogers and co-workers reviewed the progress which they had made in evaluating fermentations using Z. mobilis. The medium they used had the composition given in Table 1.

TABLE 1

| Component | Amount (g/l) |
| --- | --- |
| glucose | 100 |
| yeast extract | 5 |
| $(NH_4)_2SO_4$ | 1 |
| $KH_2PO_4$ | 1 |
| $MgSO_4 7H_2O$ | 0.5 |

In passing, mention was made that good productivities and half-life periods were demonstrated with immobilized cell reactors. The mode of immobilization was not apparent. When we attempted an actual fermentation using cells of Z. Mobilis immobilized by our techniques, we found that appreciable gas was evolved during growth of the bacteria and that cells tended to leak from the immobilized system out into the nutrient medium. Clearly these are disadvantages relative to the present, non-fermentative process.

More generally, the use of immobilized cells has appreciable advantages over the more usual use of free cells. A continuous process is facilitated, less power is required relative to that for fermentation, and a higher cell density is possible. The present process is especially suited to continuous operation: the cells are retained in the reactor and are not lost to contaminate the product stream; there is no need for cell separation. Furthermore, since the medium is nutritionally deficient, there is less risk of contamination by other microorganisms and there is no need to employ strictly sterile equipment.

It will also be appreciated that the use of ethanol-producing bacteria leads to improvements compared with the use of yeasts. In particular, when compared with the yeast Saccharomyces carlsbergenisis, bacteria such as Zymomonas mobilis have a higher rate of specific glucose uptake (2.6 fold increase in glucose uptake, also a 2.9 fold in ethanol production) and use a more efficient metabolic pathway (Swings J. and De Ley J. (1977) Bact. Reviews, 41, 1–46).

For best results in the process of the invention, the cells of the ethanol-producing bacterium should be immobilized by entrapment within a substrate-permeable material. This form of immobilization is particularly suited to the anaerobic bacteria such as Z. mobilis since it is then easier to maintain a local environment for the bacterial cells which has a suitably low oxygen concentration. The immobilization can be carried out in a manner known per se, and is preferably carried out by the entrapment of the bacterial cells within a gel.

Suitable gel materials include alginate, polyacrylamide, agar, xanthan gum/locust bean gum, kappa-carrageenan or kappa-carageenan/locust bean gum.

Of these gel materials, we find an alginate gel, in particular a calcium alginate gel, is most satisfactory. Other alginate gels can be used, such as those formed with other group II metals, but we much prefer calcium alginate. In this way, the cells are trapped in an inert, three-dimensional polymer network with relatively large interstitial spaces in the gel.

For immobilization of the bacterial cells in alginate gel, we prefer first to slurry the cells with an aqueous solution of a soluble alginate for example sodium alginate. The concentration of cells in the slurry is in no way critical to the success of the present process, but by trying various concentrations an optimum can readily be found for a particular system. Typically the concentration of cells is between 1 and 90% wet weight- /volume (ww/v), although preferably it is from 10 to 40% ww/v, more preferably about 20% ww/v. Equally, the concentration of soluble alginate is not critical. A particularly suitable concentration is between 1 and 20% w/v, more especially between 0.5 and 10% w/v, e.g. 2% w/v.

The resultant slurry of cells in alginate is then metered into a solution of a metal salt with which the soluble alginate forms a gel. As mentioned, the preferred gel is calcium alginate, and suitable salts then include calcium chloride. In particular, we prefer to use a calcium chloride solution whose molarity is from 0.01 to 1 M, more preferably from 0.05 to 0.5 M, most preferably around 0.1 M. The metal salt solution is preferably at 15°–40° C., more especially around 30° C., as the slurry is metered in, and it is also advantageous if the solution is stirred. The stability of the product is enhanced if the metal salt solution further contains some dissolved glucose, e.g. 5 to 20% (w/v) glucose, preferably about 10% (w/v) glucose.

By metering in the slurry as discrete droplets, it is a simple matter to produce perfectly spherical pellets of gel entrapping the cells. The pellet size can be varied, but for ease of handling and for efficient mass transfer properties in use, it is preferred to generate pellets which are about 3 to 5 mm in diameter. It is readily possible also to immobilize the cells in a block of gel (which is then divided for use) or in rope of gel (which for use can be wound on a former or cut into sections). Generally, the large immobilized pellets or other shapes are preferred with anaerobic bacteria since inward oxygen diffusion is low.

Similar techniques can be used for immobilizing the cells in other gel systems. Procedures for forming gelled products are available in the literature, and it is a simple matter to adapt them to the present purposes.

If desired, the enzyme system can be co-immobilized with other materials, particularly but not exclusively inert materials. An inert material can act as a core, and more generally can impart desirable properties to the product.

Preferably any inert material which is used consists of particles with dimensions of from 250 to 1500 microns. A maximum dimension less than about 150 microns is undesirable if the product is to be used in a fluidized bed reactor.

Examples of inert materials which can be used include porous particles of either naturally-occurring or manufactured materials.

Bone char, otherwise known as bone black, bone charcoal or animal charcoal, is a particularly suitable inert material for the present invention. Bone char offers a combination of advantageous properties which is not met by the materials which have previously been suggested for use as support material.

Bone char is obtained at an economically favourable cost from a naturally-occurring raw material, and consists principally of a hydroxyapatite structure over which there is a thin, evenly-dispersed coating of active carbon, with the particles being of an irregular form and providing a suitable 'key' for adhesion of the external deposit. In addition, it has been used for many years in sugar refining throughout the world, and it is well established that its use entails no hazardous problems in the food industry. It exhibits a good degree of thermal stability and ordinarily contains no artificial additives which might give rise to further problems even when used in midly acidic conditions.

The particle size of the bone char is not critical for a successful immobilization. We refer to use particles with a minimum dimension of less than 2 mm, more preferably less than 1 mm, and with a maximum dimension of less than 6 mm, more preferably less than 2 mm.

After formation of the gel-immobilized product, the gel can be dried. The dried products may be prepared for example by drying the gel to less than 70% of the original volume, preferably to less than 50% of the original volume, and more preferably to less than 40% of the original volume.

Despite the loss of water occasioned by the drying, the dried, cell-containing gels retain enzyme activity. Often the activity of the gel will be less after drying when expressed in terms of amount of substrate which is converted in unit time by a given sample of gel. On the other hand, the reduction in gel volume will usually mean that the activity per unit volume will be greater after drying. Some uptake of water may occur when the dried gels of the invention are used to effect an enzyme-catalysed reaction in aqueous solution, but normally some reduction in gel volume is maintained. Thus the increase in activity per unit volume is normally maintained.

Apart from retention of enzyme activity, the dried gels have other beneficial properties. Thus, they are typically stronger, more resistant to compression and abrasion, and easier to handle and to transport. Moreover, they represent a very convenient way in which enzymatically-active cells may be stored prior to use.

The drying technique is not particularly critical, though simple air drying at or near room temperature using a current of air appears to give the best results. Freeze-drying can be used, though there is often a greater loss in enzyme activity than with air drying and moreover the reduction in volume may not be substantial. Drying in a vacuum oven and drying through dewatering using ethanol exchange are also possible, though again there will usually be a greater loss in activity than with air drying.

Air drying is suitably effected at 20° to 50° C. for 1 to 20 hours, with 2 to 5 hours at 30° to 35° C. representing preferred conditions. Gentle turning over of the gel during drying is helpful, as also is the use of air with low humidity.

The dried gel preferably has a volume less than 70% of that of undried gel, and preferably weighs less than 70% of the undried gel.

The retention of enzymatic activity after drying is sometimes enhanced if the gel contains a solute or substrate. Such additives can also be used to modify the stability of the dry product, and may be incorporated during the formation of the gel. To give one example, sucrose is a solute which can beneficially be added to the metal salt solution (usually a calcium salt) during formation of an alginate gel.

The cells employed in the immobilization are preferably of an ethanol-producing microorganism of the genus Zymomonas. Bacteria of other genera can be utilized. Of the species belonging to the genus Zymomonas, we prefer *Z. mobilis*. Especially suitable strains of *Z. mobilis* include those deposited at the American Type Culture Collection under the Accession Numbers ATCC 10988 and ATCC 29501.

Processes in accordance with the present invention are preferably carried out as a continuous process, suitably by loading the immobilized cells in to a column and passing the substrate as a solution through the column.

Notwithstanding the preference for continuity, the present process can also be performed batch-wise.

Whereas the known fermentations of *Z. mobilis* employ a glucose-based nutrient medium to provide the substrate, the present process employs a nutritionally deficient medium containing glucose or other substrate such as fructose or sucrose. For most purposes, we prefer to use an aqueous solution of a carbohydrate alone, without any other nutrients or assimilable materials. More specifically, we prefer to use an aqueous solution of glucose containing from 5 to 20% (w/v) glucose, more preferably a solution of about 10% glucose.

It was surprising to discover that with ethanol-producing bacteria, the conversion of glucose or other carbohydrate to ethanol could be effected using a nutritionally deficient medium, such that appreciable growth of the bacterium does not occur during ethanol production. The available literature concerning ethanol-producing bacteria always describes the use of media permitting growth of the bacterium. Moreover, with yeasts it is now known that ethanol production is possible with immobilized systems but only when a balanced medium is supplied. In this respect, reference is made to an article by Wada et al concerning immobilization of yeast cells with carrageenan gel (European J. Appl. Microbial. Biotechol. 8,241-247 (1979)): at page 246 it is explained "The supply of nutrient medium for growth was essential for continuous production. The depletion of nutrients caused death of cells and decrease of productivity".

The present invention is illustrated by the following non-limiting examples, were 'ww' indicates a wet weight of cells (dry weights being about one-fifth the figure):

EXAMPLES 1 to 7

*Zymomonas mobilis* ATCC 10988 was inoculated in 500 ml shake-flasks containing 200 ml aliquots of medium of the composition given in Table 2 below:

TABLE 2

| Compound | Amount (g/l) |
| --- | --- |
| glucose | 100 |
| yeast extract | 10 |
| $(NH_4)_2SO_4$ | 1 |
| $KH_2PO_4$ | 1 |
| $MgSO_4 7H_2O$ | 0.5 |
| dilute acid | to pH 5 |

The flasks were then briefly degassed using a vacuum line, sealed in polythene bags, and incubated with minimal agitation at 30° C.

After 70 hours, the pH had fallen to 3.85. The cell concentration was then 7 gww/l with a yield of 0.07 gww/g glucose supplied. Cells were harvested using centrifugation at 12000 rpm for 15 minutes at 30° C. The harvested mass of cells from the centrifuge was slurried with 5% (w/v) sodium alginate solution to give a 20% (ww/v) slurry. Pellets containing the cells were then formed by extruding the slurry in 0.1 M calcium chloride containing 15% (w/v) glucose.

The pellets were then assayed in batch by shaking in substrate solutions at 30° C., or continuously by packing into columns, thermostatted at 30° C., with the substrate pumped up the column. Ethanol and remaining glucose were measured by chemical assay. The theoretical maximum yield of ethanol/g glucose is 55% and in all cases the mass balance was completed on the basis that any deficiencies were due to unused glucose.

Batch Assays

Measurements were taken when the ethanol concentration was around 50 g/l. The activities of the immobilized cells assayed with various substrate solutions were as follows in Table 3:

TABLE 3

| Example No. | Substrate | Activity (g ethanol/gww/h) |
| --- | --- | --- |
| 1 | 100 g/l glucose | 0.49 |
| 2 | 175 g/l glucose | 0.38 |
| 3 | 250 g/l glucose | 0.53 |
| 4* | growth medium (100 g/l glucose) | 0.51 |

*Example 4 is a comparison example.

Cell leakage was observed when the growth medium of Table 2 was used in Example 4 as the substrate, due to cell growth inside the pellets.

Continuous assays

Substrate was pumped through the column at a constant rate of about 0.085 ecv/h. There was typically a lag time of about one day before equilibrium was reached. The activities were then measured, giving the results shown in Table 4:

TABLE 4

| Example No. | Substrate | Activity (g ethanol/gww/h) |
| --- | --- | --- |
| 5 | 100 g/l glucose | 0.47 |
| 6 | 250 g/l glucose | 0.33 |

The half-life for the activity was about 90 h. No gas accumulation was observed in the column, nor was any disruption of the pellets. Moreover, microscopic examination of pellets in cross-section before and after use showed that no division of the cells occurred during use. As with the batch experiments, when a complete growth medium was used as substrate, it was noticed that the product liquid contained cells of the bacterium, these cells arising from growth of the immobilized cells.

EXAMPLE 7

Pellets were dried with a stream of air at ambient temperature. Typically 22% of the original activity was lost by drying to 35% of the original weight. Pellets dried to 45% of original weight lost 73% of their activity after 288 h storage in a sealed container at room temperature.

Dried pellets were packed in a column. Under this mode of operation the initial activity of the cells, using 250 gl$^{-1}$ glucose as substrate, was reduced to 45% of that of the equivalent column of undried pellets.

EXAMPLE 8

The procedure of Examples 1 to 7 was repeated except that the harvested mass of cells was slurried together with bone char, sieved to 25 to 46 mesh, in the solution of sodium alginate, thereby giving 20% (ww/v) of cells and 20% (dry w/v) of bone char. The slurry was then extruded as before, giving pellets containing bone char particles.

When assessed on a continuous basis, the activity of the immoblized cells was substantially the same as the pellets without bone char. However, the pH of the eluate was increased.

EXAMPLE 9

Cells of *Z. mobilis* ATCC 10988 were immobilized in kappacarageenan by mixing the wet cells with a 4.5% w/v carageenan solution in phosphate-buffered saline at 50° C. so as to give a final cell concentration of 20% v/v cells. The slurry was then extruded drop-wise into a 0.3M potassium chloride bath at 10° and incubated for 4 hours.

The resultant immobilized cells were assayed on a continuous basis against 100 g/l glucose solution. The activity was 0.32 g ethanol/gww cells/hour. Again there was the advantage that the converted solution was cell-free.

EXAMPLE 10

Example 6 was repeated using a glucose-fructose mixed solution containing 250 g/l of total sugar. The activity was 0.187 g ethanol/gww/hour.

I claim:

1. A process for producing ethanol, wherein a carbohydrate is converted by immobilized cells of an ethanol-producing bacterium into ethanol, said carbohydrate being presented to said cells in a medium which is nutritionally inadequate for growth of said cells by lacking at least one factor required therefor.

2. The process of claim 1, wherein said cells are immoblized in a gel.

3. The process of claim 2, wherein said gel is dried after immobilization of said cells.

4. The process of claim 2, wherein said cells are co-immobilized with bone char.

5. The process of claim 1 wherein said carbohydrate is employed in aqueous solution which does not contain any other nutrient or assimilable material.

6. The process of claim 5 wherein said aqueous solution contains 5–20% (w/v) glucose.

7. The process of claim 6 wherein said solution contains about 10% glucose.

8. The process of claim 6 wherein said cells are immobilized in a calcium alginate gel.

9. The process of claim 6 wherein said cells are immobilized in a calcium alginate-bone char gel.

10. In a process for producing ethanol by conversion of a substrate using cells of a bacterium, the improvement which comprises immobilizing said cells and converting said substrate in a non-fermentative manner by dissolving said substrate in water to give a medium which lacks at least one factor required for growth of the bacterium, and contacting said medium with said immobilized cells to effect said conversion.

11. The process of claim 10, when effected on a continuous basis.

12. The process of claim 10 wherein said substrate is a carbohydrate and said medium lacks any other nutrient or assimilable material.

13. The process of claim 12 wherein said carbohydrate is glucose in an amount of 5–20% (w/v).

14. The process of claim 13 wherein said amount is about 10%.

15. The process of claim 13 wherein said cells are immobiled in a calcium alginate gel.

16. The process of claim 13 wherein said cells are immobilized in a calcium alginate-bone char gel.

* * * * *